United States Patent [19]

Frank

[11] 4,249,017

[45] Feb. 3, 1981

[54] TRIS(N-CARBALKOXYLAMINOMETHYL)-PHOSPHINE OXIDES AND SULFIDES

[75] Inventor: Arlen W. Frank, Slidell, La.

[73] Assignee: The United States of America as represented by the Secretary of Agriculture, Washington, D.C.

[21] Appl. No.: 964,852

[22] Filed: Nov. 29, 1978

[51] Int. Cl.³ .................. C07C 125/077; C07C 161/00
[52] U.S. Cl. ...................................... 560/148; 8/183; 8/185; 8/187; 560/158
[58] Field of Search .............................. 560/148, 158

[56] References Cited

U.S. PATENT DOCUMENTS

| | | | |
|---|---|---|---|
| 3,159,667 | 12/1964 | Peters | 562/594 |
| 3,784,638 | 1/1974 | Lambert | 562/592 |
| 4,150,242 | 4/1979 | Wilson | 562/594 |

*Primary Examiner*—Vivan Garner
*Attorney, Agent, or Firm*—M. Howard Silverstein; Raymond C. Von Bodungen; David G. McConnel

[57] ABSTRACT

The title compounds, having the formula $(RO_2CNHCH_2)_3PY$ where Y=oxygen or sulfur, are prepared by reacting a tris(N-carbalkoxylaminomethyl)phosphine, having the formula $(RO_2CNHCH_2)_3P$, with an oxidizing or sulfurizing agent. The products, after methylolation with formaldehyde, are useful as finishing agents for imparting flame retardant properties to cotton fabrics.

3 Claims, No Drawings

TRIS(N-CARBALKOXYLAMINOMETHYL)PHOSPHINE OXIDES AND SULFIDES

CROSS REFERENCE TO RELATED APPLICATIONS

Ser. No. 964,751, filed Nov. 29, 1978, U.S. Pat. No. 4,204,072 —"TRIS(N-CARBALKOXYLAMINOMETHYL)PHOSPHINES"

Ser. No. 964,853, filed Nov. 29, 1978, U.S. Pat. No. 4,171,448—"QUATERNARY PHOSPHONIUM SALTS BEARING CARBAMATE GROUPS"

BACKGROUND OF THE INVENTION (1) Field of the Invention

This invention relates to novel tris(N-carbalkoxylaminomethyl)phosphine oxides and sulfides and to methods for preparing the same.

(2) Description of the Prior Art

Nowhere in the prior art do there exist tertiary phosphine oxides and sulfides containing carbamate groups attached to each of the phosphorus substituents through its nitrogen atom.

Furthermore, the preparation and properties of such compounds, together with methods for their methylolation, and their application to cotton fabrics for the purpose of imparting flame retardant properties to the cotton, has not been known previously.

SUMMARY AND OBJECTS OF THE INVENTION

The instant invention discloses as new compounds tris(N-carbalkoxylaminomethyl)phosphine oxides and sulfides having the formula $(RO_2CNHCH_2)_3PY$, where R is an alkyl radical having from 1 to 6 carbon atoms and Y is selected from the group of oxygen and sulfur, and the processes for producing said compounds.

It is the principal object of this invention to prepare novel tris(N-carbalkoxylaminomethyl)phosphine oxides and sulfides by methods which prevent interaction of products and by-products.

It is another object of the invention to prepare derivatives of tris(N-carbalkoxylaminomethyl)phosphine oxides and sulfides that are useful as finishing agents for cotton textile fabrics, giving fabrics with improved flame resistance properties. Other objects and improvements of this invention will become obvious from the description of the preferred embodiments.

DESCRIPTION OF THE PREFERRED EMBODIMENTS

The novel compounds of this invention have the general formula $(RO_2CNHCH_2)_3PY$, where R is an alkyl or substituted alkyl radical having from 1 to 6 carbon atoms, and Y is selected from the group of oxygen and sulfur.

In accordance with the practice of this invention, the new compounds are prepared by reacting a tris(N-carbalkoxylaminomethyl)phosphine having the formula $(RO_2CNHCH_2)_3P$, where R is as defined above, with an oxidizing or sulfurizing agent, and recovering the product from the resulting reaction mixture.

The tris(N-carbalkoxylaminomethyl)phosphines, themselves novel substances, are prepared as described in my co-pending application Ser. No. 964,751, TRIS(N-CARBALKOXYLAMINOMETHYL)-PHOSPHINES. Examples of such substances are tertiary phosphines in which R is methyl, ethyl, isopropyl, 2-methoxyethyl, n-butyl, and the like.

The oxidizing agents employed in the practice of this invention comprise gases such as air, oxygen, oxides of nitrogen including nitric oxide and dinitrogen tetroxide, sulfur dioxide, and the like, inorganic substances such as hydrogen peroxide, mercuric oxide, potassium permanganate, chromic acid, and the like, and organic substances such as alkyl hydroperoxides, peroxy acids, diacyl peroxides, epoxides, ozonides, and the like.

The sulfurizing agents employed in the practice of this invention comprise elemental sulfur, inorganic substances such as sodium polysulfide, ammonium sulfide, mercuric sulfide, thiophosphoryl chloride, thiocyanogen, and the like, and organic substances such as mercaptans, episulfides, thionocarbonates, dialkyl disulfides, and the like.

The reaction between the tris(N-carbalkoxylaminomethyl)phosphine and the oxidizing or sulfurizing agent is most conveniently carried out in the presence of a solvent such as water, ethanol or acetone, but may also be performed in the absence of a solvent. The molar ratio may be varied from 10:1 to 1:10, the preferred ratio being 1:1. The temperature may be varied from 0° C. to 100° C., depending on the strength of the oxidizing or sulfurizing agent and the physical properties of the solvent. The pressure may be atmospheric, subatmospheric or higher than atmospheric. If the tertiary phosphine is air-sensitive, as is often the case, the reaction may be carried out in an atmosphere of an inert gas such as nitrogen or argon.

If the base used in the preparation of the tris(N-carbalkoxylaminomethyl)phosphine is a preferred base of the type disclosed in my co-pending application Ser. No. 964,751, TRIS(N-CARBALKOXYLAMINOMETHYL)PHOSPHINES, i.e. a base capable of trapping the by-product formaldehyde or formaldehyde derivative, the tertiary phosphine need not be isolated and purified. In such a case, the oxidizing or sulfurizing agent can be added directly to the reaction mixture containing the base and the tertiary phosphine. The consequence is a considerable saving of time and effort. Illustrations of this technique are given in Examples 4, 5 and 6.

If the base used in the preparation of the tris(N-carbalkoxylaminomethyl)phosphine is not a preferred base, as defined in the preceding paragraph, the subsequent oxidation or sulfurization yields a product distinctly different from that obtained through the use of a preferred base. This is illustrated in Example 7, where the base is sodium hydroxide. The product of Example 7 is a colorless oil, whereas that of Example 4, employing the same quaternary phosphonium salt, is a high-melting crystalline solid. Their spectra, solubility and other physical properties are also different. Efforts to interconvert the products by reaction of the crystalline product with methyl N-hydroxymethylcarbamate in the presence or absence of sodium hydroxide catalyst, or by treatment of the liquid product with ammonium hydroxide, were not successful.

Melting points are corrected. Elemental analyses were performed by commercial laboratories. IR spectra were taken on a Perkin-Elmer 137B with NaCl optics (w=weak, m=medium, s=strong, vs=very strong). $^1H$ NMR spectra were taken on a Varian HA-60-IL at 24.3 MHz, using 85% $H_3PO_4$ as an external reference (s=singlet, d=doublet, t=triplet, m=multiplet).

Chemical shifts downfield of the reference are positive in both cases.

EXAMPLE 1

This example illustrates the preparation of tris(N-carbomethoxylaminomethyl)phosphine oxide, $(CH_3O_2CNHCH_2)_3PO$, hereinafter referred to as TMPO, from tris(N-carbomethoxylaminomethyl)phosphine, $(CH_3O_2CNHCH_2)_3P$, hereinafter referred to as TMP.

A 30% solution of hydrogen peroxide (57.0 g, 0.5 mol) was added dropwise to a vigorously stirred slurry of 147.6 g (0.5 mol) of TMP in 500 ml of acetone under an argon atmosphere. Ice-bath cooling was applied as necessary to counter the strongly exothermic reaction. The TMP gradually dissolved, and was all in solution when two-thirds of the peroxide had been added. About 10 min. after the addition was completed, the product started to crystallize. Next day, the solid was collected on a filter, washed with acetone and dried, giving 98.9 g (63.5% yield) of TMPO, mp 179°–180° C. Work-up of the filtrate raised the yield to 126.0 g (81.0% yield). Two recrystallizations from ethanol afforded pure TMPO as a white, crystalline solid, mp 189°–190° C. IR (Nujol): 780m, 830w, 852m, 972w, 1015m, 1135m, 1145m, 1160m, 1190m, 1260s, 1300m, 1540s (NH, amide II), 1710vs br (C=O, amide I), 3250w (NH, bonded) and 3400w (NH, free) cm$^{-1}$. $^1$H NMR (DMSO-d$_6$): δ 3.60 (s, CH$_3$), 3.47 (t, CH$_2$, J=9.0 Hz, blending into the CH$_3$ peak with D$_2$O; combined CH$_3$ and CH$_2$, 15H), and 7.34 (m, 3H, NH, vanishing with D$_2$O) ppm.

Anal. Calcd for $C_9H_{18}N_3O_7P$: C, 34.73; H, 5.83; N, 13.50; P, 9.95. Found: C, 34.69; H, 5.70; N, 13.48; P, 10.00.

The phosphine oxide TMPO is soluble in chloroform and insoluble in water, acetone, and the common organic solvents. It can be recrystallized from ethanol (25 ml/g) or water. When heated above its melting point, it gasses without discoloration and froths to a tan-colored resin at 260° C.

EXAMPLE 2

Hydrogen peroxide (30%) was added dropwise to a well-stirred slurry of 1476.2 g (5 mols) of TMP in 2000 ml of water under an argon atmosphere, with ice-bath cooling applied as needed to maintain the reaction temperature between 20 and 30° C. The addition was stopped after 3.5 hr, when 550.6 g (4.85 mols) of 30% hydrogen peroxide had been added. At this point, an iodine test for unreacted TMP was negative, and the product, which had separated during the reaction, abruptly foamed to the surface. The product was collected on a filter, rinsed with water and air-dried, giving 826.6 g (53.1% yield) of crystalline TMPO, mp 179°–180° C.

EXAMPLE 3

This example illustrates the preparation of tris(N-carbomethoxylaminomethyl)phosphine sulfide, $(CH_3O_2CNHCH_2)_3PS$, hereinafter referred to as TMPS, from TMP.

A mixture of 2.95 g (0.01 mol) of TMP, 0.32 g (0.01 g-atom) of sulfur and 25 ml of benzene was heated to reflux under an argon atmosphere. After 1 hr, most of the solids had dissolved. The mixture was cooled and stripped of benzene under reduced pressure. The residue was taken up in hot acetone, filtered hot to remove the unreacted sulfur (0.12 g), and stripped again under reduced pressure, leaving 2.40 g (73.4% yield) of TMPS as a white, crystalline solid. Two recrystallizations from ethanol afforded pure TMPS, mp 136.5°–137° C. IR (Nujol): 772w, 780w, 790w, 810w, 846m sh, 855s, 970m, 1015s br, 1145s, 1190s, 1240vs, 1290vs, 1520vs br (NH, amide II), 1710vs and 1740s (C=O, amide I), and 3400s (NH) cm$^{-1}$. $^1$H NMR (DMSO-d$_6$): δ 3.61 (s, CH$_3$), 3.72 (t, CH$_2$, J=3.0 Hz, collapsing with D$_2$O to d, J=3.0 Hz; combined CH$_3$ and CH$_2$, 15H), and 7.39 (m, 3H, NH, vanishing with D$_2$O) ppm. $^{31}$P NMR (DMSO): δ 48.5 ppm.

Anal. Calcd. for $C_9H_{18}N_3O_6PS$: C, 33.03, H, 5.54; N, 12.84; P, 9.46; S, 9.80. Found: C, 33.08; H, 5.49; N, 12.82; P, 9.60; S, 9.80.

The phosphine sulfide TMPS is soluble in chloroform, and insoluble in water or ethanol. It can be recrystallized from ethanol (6 ml/g), 2-propanol or water.

EXAMPLE 4

This example and the two which follow illustrate the use of a preferred base, ammonium hydroxide, in the preparation of TMPO or TMPS from tetrakis-(N-carbomethoxylaminomethyl)-phosphonium chloride, $(CH_3O_2CNHCH_2)_4PCl$ (TMPC), or octakis(N-carbomethoxylaminomethyl)diphosphonium sulfate, $[(CH_3O_2CNHCH_2)_4P]_2SO_4$ (OMPSf).

Conc. ammonium hydroxide (10 ml) was added to a well-stirred slurry of 20.94 g (0.05 ml) of TMPC in 100 ml of water in an apparatus previously purged with argon. The mixture gradually thickened. After 2 hr. the mixture, still containing the excess base and the by-products, was treated dropwise with 5.67 g (0.05 mol) of 30% hydrogen peroxide over a 20 min. period, with ice-bath cooling applied as needed to keep the temperature below 30° C. Next day, the mixture was stripped to dryness in a rotary evaporator, triturated with ethanol and filtered, giving 13.69 g (88.0% yield) of crystalline TMPO, mp 176°–178° C.

TMPC is not oxidized by hydrogen peroxide in the absence of a base.

EXAMPLE 5

An identical experiment in which the excess base and byproducts were removed prior to oxidation gave 13.91 g (89.4% yield) of crystalline TMPO, mp 174°–177° C.

EXAMPLE 6

Conc. ammonium hydroxide (500 ml) was added to a solution of 1078.4 g (1.25 mol) of OMPSf in 1500 ml of water in an apparatus previously purged with argon. TMP started to separate within minutes. After 2 hr. the mixture, still containing the excess base and the by-products, was treated dropwise with 977 g (2.87 mol) of 20% ammonium sulfide over a 2 hr. period at 25°–30° C. Next day, the product was collected on a filter, rinsed thoroughly with water and air-dried, giving 521.4 g of crude TMPS, mp 120°–125° C. One recrystallization from ethanol gave 398.3 g (48.9% yield) of crystalline TMPS, mp 132°–135° C.

EXAMPLE 7

This example illustrates the effect of using a base—sodium hydroxide, which is not one of the preferred bases—on the preparation of TMPO from TMPC.

A slurry of 20.94 g (0.05 mol) of TMPC in 50 ml of water was treated dropwise with a solution of 2.00 g (0.05 mol) of sodium hydroxide in 25 ml of water. During the addition, which took 5 min, the mixture cleared, turned milky, and cleared again. After 15 min, the solution was extracted with chloroform, and the chloroform extract filtered and stripped. The residue (16.79 g), a viscous, colorless oil which, unlike TMP, could not be induced to crystallize, was dissolved in 100 ml of acetone and treated dropwise with 5.70 g (0.05 mol) of 30% hydrogen peroxide over a 5 min period. The temperature rose to 40° C., and at the end an iodine test for unreacted tertiary phosphine was negative. The solution was stripped of acetone in a rotary evaporator, taken up in chloroform, extracted with water to remove any remaining peroxide, filtered, and stripped again, giving 14.00 g (62% yield) of the tertiary phosphine oxide as a colorless oil, $n_D^{20}$ 1.4962. IR (neat): 775w, 1005w br, 1055w, 1150m, 1190m, 1250s, 1290m sh, 1530s (NH, amide II), 1710vs (C=O, amide I), and 3350m (NH) cm$^{-1}$. $^1$H NMR (CDCL$_3$): $\delta$ 3.7–3.9 (m, 12H, CH$_3$), 3.9–4.6 (m, 8H, PCH$_2$), 6.63 (m, 2H, NH), and 8.13 (m, 1H, NH) ppm. $^{31}$P NMR (CHCl$_3$): $\delta$ 45.3 ppm. The elemental analyses (N, 10.82; P, 5.98) clearly showed a 4:1 molar ratio of nitrogen to phosphorus, as opposed to 3:1 in TMPO.

The product was soluble in water, ethanol, acetone and chloroform, and insoluble in ether, carbon tetrachloride, ethyl acetate and benzene.

METHYLOLATION OF THE PRODUCTS

The novel tris(N-carbalkoxylaminomethyl)phosphine oxides and sulfides of this invention each contain three NH groups which are available for reaction with crosslinking agents such as formaldehyde, glyoxal, and the like. The reaction of TMPO with formaldehyde is illustrated by the following equation:

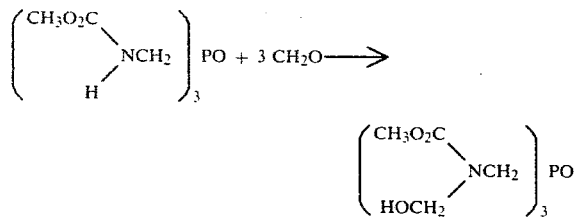

TMPO is insoluble in 37% formalin solution, but in the presence of an acid or base catalyst the TMPO dissolves, giving a mixture of N-methylol derivatives in which the trimethylol derivative is predominant. If the catalyst is a base, such as sodium hydroxide or disodium phosphate, the reaction may be carried out at room temperature (about 25° C.), with warming to 60° to 80° C. if desired; no TMPO separates when the solution is neutralized, even if no warming has been applied. If the catalyst is an acid, such as hydrochloric acid, the reaction mixture must be heated briefly to about 75° C., whereupon the TMPO dissolves, giving the same mixture of products as the base-catalyzed reaction. There is no evidence of crosslinking, i.e. formation of N—CH$_2$—N links between carbamate residues, of the kind encountered in the acid-catalyzed condensation of formaldehyde with unsubstituted carbamates (J. F. Walker, "Formaldehyde", Reinhold Publishing Corp., New York, 3rd ed., p. 391).

The N-methylol derivatives, though stable in aqueous solution, are not stable in alcohol solution. Dissociation occurs within a few hours in ethanol or a few minutes in methanol, regenerating crystalline TMPO. This precludes the use of alcohols as solvents for the methylolation of TMPO, and explains why efforts to prepare methoxymethyl derivatives of TMPO by reaction with paraformaldehyde in methanol were unsuccessful. Competition for formaldehyde evidently favors the alcohol (hemiacetal formation) in alcohol solutions and TMPO (methylolation) in aqueous solution, and suggests that, as a nucleophile, TMPO is stronger than water but weaker than alcohols.

It may be noted in passing that a similar dissociation occurs when attempts are made to recrystallize methyl N-methylolcarbamate, CH$_3$O$_2$CNHCH$_2$OH, from alcohols such as 2-propanol or t-butanol.

Attempts to measure the extent of methylolation of TMPO by the sulfite method (Walker, op. cit., p. 486) were unsuccessful. Cleavage of formaldehyde from the methylolated TMPO occurred even under the least favorable conditions, i.e. in ice-cold acid, using the procedure described by J. D. Reid, R. M. Reinhardt and J. S. Bruno, Amer. Dyestuff Rep., 54, P485-91 (1965).

Methylolated TMPO does not appear to react with gaseous ammonia, ammonium hydroxide or dimethylamine, but does react with urea or dimethylolurea giving insoluble, polymeric products.

EXAMPLE 8

A slurry of 6.22 g (0.02 mol) of TMPO and 8.11 g (0.10 mol) of 37% formalin in 25 ml of water was treated with 10 drops of 0.1 N sodium hydroxide, stirred until the TMPO dissolved, and then heated for 10 min at 80° C. to complete the reaction. After cooling, the solution was stripped on a rotary evaporator and dried under vacuum, giving 8.27 g (103.1% yield) of colorless oil, $n_D^{20}$ 1.5008. IR (neat): 774m, 875m, 970w, 1015s, 1040s, 1110m, 1160s br, 1250s, 1280s, 1540m, (NH, amide II), 1710 vs (C=O, amide I), and 3400s (OH) cm$^{-1}$. The NH absorption was greatly diminished, relative to C=O. $^1$H NMR (DMSO-d$_6$): $\delta$ 3.66 (s, CH$_3$), 3.9 (m, PCH$_2$), 4.7 (m, OCH$_2$), and 5.9 (t, OH), together with a little unreacted formaldehyde and TMPO.

EXAMPLE 9

TMPO (6.22 g, 0.02 mol) was added in portions to 4.87 g (0.06 mol) of 37% formalin solution buffered to pH 8 with 0.20 g of disodium phosphate dodecahydrate and 2 drops of 0.1 N sodium hydroxide. After the addition, the solution was heated briefly to boiling to complete the reaction, cooled, stripped on a rotary evaporator and dried under vacuum, giving 7.69 g (95.9% yield) of methylolated TMPO, identical (IR) to the product of Example 8.

EXAMPLE 10

A slurry of 6.22 g (0.02 mol) of TMPO and 4.87 g (0.06 mol) of 37% formalin in 10 ml of water was treated with 5 drops of conc. hydrochloric acid, stirred 1.5 hr. and then heated briefly to 75° C., whereupon the TMPO dissolved. After cooling, the solution was stripped on a rotary evaporator and dried under vacuum, giving 8.07 g (100.6% yield) of colorless oil, $n_D^{20}$ 1.4980, identical (IR,NMR) to the product of Example 8.

EXAMPLE 11

A solution of 8.22 g (0.02 mol) of the product of Example 7 and 8.11 g (0.10 mol) of 37% formalin in 25 ml of water was made alkaline to pH 9 with 10% sodium hydroxide, allowed to stand overnight, stripped on a rotary evaporator and dried under vacuum, giving 9.25 g (94.7% yield) of colorless oil. IR (neat): 772m, 1020s, 1110m, 1170s, 1190s, 1250s, 1535m (NH, amide II), 1700vs (C=O, amide I), and 3400s (OH) cm$^{-1}$. The NH absorption was greatly diminished relative to C=O.

APPLICATION OF THE PRODUCTS TO COTTON

Carbamates are employed extensively in the textile industry to impart durable press properties to cotton fabrics (H. F. Mark, N. S. Wooding and S. M. Atlas, "Chemical After-treatment of Textiles", Wiley-Interscience, New York, 1971, pp. 417–64). Some attempts have been made to incorporate phosphorus in these finishes to also impart flame retardant properties to the cotton fabrics, without notable success (W. A. Reeves and R. M. Perkins, Colourage Annual 1 [1971]).

In a companion application, Ser. No. 964,853, QUATERNARY PHOSPHONIUM SALTS BEARING CARBAMATE GROUPS, I have shown how to prepare novel quaternary phosphonium salts bearing one or more carbamate groups attached through nitrogen, and have demonstrated the usefulness of these phosphonium salts as finishing agents for cotton. In the paragraphs that follow, I shall disclose the techniques that may be applied to the novel compounds of this invention to render them useful as finishing agents for cotton.

The novel tris(N-carbalkoxylaminomethyl)phosphine oxides and sulfides of this invention each contain nitrogen and phosphorus, the two elements that are considered necessary and sufficient for imparting flame retardant properties to cotton fabric. The elements, moreover, are in the ratio of 3 parts nitrogen to 1 part phosphorus that is considered to be optimum for flame retardant efficiency, and the phosphorus is in a form that needs no further stabilization.

For practical purposes, it is also desirable that the flame retardant finish be durable to laundering. To this end, methods are given for chemically binding the novel compounds to the cotton cellulose through the use of cross-linking agents such as formaldehyde. Examples 12 to 17 illustrate the application of TMPO to cotton printcloth, with formaldehyde as the binding agent. The TMPO is first methylolated, as disclosed in the preceding section, and is then caused to react with the cotton cellulose by curing at an elevated temperature in the presence of a catalyst. The catalyst, it may be noted, can be either an acid or a base. Example 18 illustrates the application of this finish to cotton sateen. Examples 19 to 23 illustrate the application of TMPO to cotton printcloth with urea, melamine or their methylol derivatives as co-reactants.

The flammability of the treated fabric was determined by the Oxygen Index (O.I.) Test, as described in the "Annual Book of ASTM Standards", American Society for Testing and Materials, Philadelphia, 1974, Part 35, p. 732, or by the Match Test, as described by W. A. Reeves and G. L. Drake, Jr., "Flame Resistant Cotton", Merrow, Watford Herts., England, 1971, p. 14. Wrinkle recovery (WRA, W+F, conditioned) was determined by the Monsanto test, as described in the "Annual Book of ASTM Standards", op. cit., Part 32, p. 226.

Phosphorus analyses were performed by the X-ray fluorescence method, nitrogen analyses by the Kjeldahl method, and formaldehyde analyses by the chromatropic acid method after digestion with sulfuric acid.

EXAMPLES 12 to 17

These examples illustrate the application of TMPO to cotton fabric with formaldehyde as the binding agent.

In each case, the padding formulation was prepared by dissolving 13.07 g (42 mmol) of TMPO in a solution of 0.20 g of sodium hydroxide in 10.23 g (126 mmol) of 37% formalin, neutralizing to pH 7 with 6N HCl, adding 12.5 mmol of the catalyst and 0.1 g of Triton X-100 (a wetting agent), and making up to 50 g with water. The final pH of each formulation is given in the table.

An 80×80 desized, scoured and bleached cotton printcloth was cut into 6"×12" swatches, immersed in one of the formulations, padded to about a 95% wet pickup, dried at 85° C. for 4 min in a forced draft oven, and cured at 160° C. for 4 min in another forced-draft oven. The swatches were then rinsed for 15 min in hot running tap water and line dried. The results for a series of such experiments with various catalysts are assembled in Table I.

The add-on was negligible in the absence of a catalyst (Example 15), but increased to 5 to 10% when either an acid or a base catalyst was added to the formulation. Sodium carbonate (Example 16) and magnesium chloride/citric acid (Example 12) gave comparable add-ons, provided that the cure time for the former was extended to 10 min. Magnesium chloride/citric acid (Example 12) gave comparable add-ons, provided that the cure time for the former was extended to 10 min. Magnesium chloride by itself (Example 14) was not sufficiently acidic to be an effective catalyst. The flame resistance (O.I.) and wrinkle resistance (WRA) both increased with add-on when the catalyst was an acid, but only the flame resistance increased when the catalyst was a base.

EXAMPLE 18

Application of the methylolated TMPO formulation to cotton sateen with magnesium chloride/citric acid catalyst, as described in Example 12, gave fabric with an 11.6% add-on and a 90° match test angle. These results were similar to those obtained with the printcloth.

EXAMPLES 19 to 23

These examples illustrate the application of TMPO to cotton fabric with urea or melamine as co-reactants, and formaldehyde as the binding agent.

In each case, the padding formulation (50 g) contained 13.07 g (42 mmol) of TMPO, 84 mmol of the co-reactant, 12.5 mmol of catalyst and 0.1 g of Triton X-100. In all but Example 20, the TMPO was methylolated with 10.23 g (126 mmol) of 37% formalin prior to addition of the co-reactant. In Examples 20 and 21, 10.07 g (84 mmol) of crystalline N,N'-dimethylolurea was substituted for the urea, and in Example 23 5.30 g (42 mmol) of melamine was substituted for the urea. The composition and final pH of each formulation are given in Table II.

With magnesium chloride as the catalyst, melamine helped to bind the methylolated TMPO to the fabric (Example 23), but urea did not (Example 22). Sodium dihydrogen phosphate, a mildly acidic catalyst, was too acidic for use with melamine, but helped urea to bind the methylolated TMPO to the fabric, especially when both the urea and the TMPO were methylolated prior to padding (Example 21). The fabrics with the highest add-on passed the match test with an angle of 110°.

The foregoing examples are given to illustrate the preparation and properties of the novel compounds of this invention, and their use as flame retardants for cotton. The examples are given merely for purposes of illustration, and should not be construed as limiting the scope of the invention.

TABLE 1

| Example | Catalyst | pH | % Add-on | % P | % N | % CH$_2$O | O.I. | WRA |
|---|---|---|---|---|---|---|---|---|
| 12 | MgCl$_2$/citric acid | 2.3 | 10.0 | 1.07 | 1.16 | 2.76 | 0.211[a] | 280 |
| 13 | Zn(NO$_3$)$_2$ | 5.5 | 8.4 | 0.86 | 0.92 | 1.34 | 0.210[a] | 252 |
| 14 | MgCl$_2$ | 6.5 | 1.5 | 0.08 | 0.13 | 0.09 | 0.183 | 207 |
| 15 | None | 7.0 | 1.0 | 0 | 0.01 | 0.17 | 0.179 | 194 |
| 16 | Na$_2$CO$_3$ | 10.7 | 6.1 | 0.73 | 0.73 | 0.06 | 0.214 | 192 |
| " | Na$_2$CO$_3$[b] | " | 9.0 | 1.05 | 1.21 | | 0.234 | 212 |
| 17 | NaOH | 11.8 | 4.3 | 0.62 | 0.62 | 0.01 | 0.204 | 192 |

[a] Match test angle 80°.
[b] Cured 10 min at 160°

TABLE II

| Ex. | Catalyst | TMPO methylolated | Urea | pH | % Add-on | % P | % N | Match angle |
|---|---|---|---|---|---|---|---|---|
| 19 | NaH$_2$PO$_4$ | Yes | No | 4.7 | 12.2 | 0.32 | 3.05 | 20 |
| 20 | MgCl$_2$ | No | Yes | 5.6 | 11.3 | 0.24 | 2.72 | 20 |
| 21 | NaH$_2$PO$_4$ | Yes | Yes | 4.9 | 35.0 | 1.50 | 4.68 | 110 |
| 22 | MgCl$_2$ | Yes | No | 6.6 | 5.8 | 0.17 | 1.04 | 0 |
| 23 | MgCl$_2$ | Yes | No[a] | 6.7 | 34.4 | 0.92 | 7.75 | 80 |

[a] Melamine

I claim:

1. Tris(N-carbalkoxylaminomethyl)phosphine oxides and sulfides having the formula (RO$_2$CNHCH$_2$)$_3$PY, where R is an alkyl radical having from 1 to 6 carbon atoms and Y is selected from the group of oxygen and sulfur.

2. The compound of claim 1 wherein the formulation is tris(N-carbomethoxylaminomethyl)phosphine oxide.

3. The compound of claim 1 wherein the formulation is tris(N-carbomethoxylaminomethyl)phosphine sulfide.

* * * * *